(12) United States Patent
Slater et al.

(10) Patent No.: US 6,264,599 B1
(45) Date of Patent: Jul. 24, 2001

(54) RADIOACTIVE THERAPEUTIC SEEDS HAVING FIXATION STRUCTURE

(75) Inventors: Charles R. Slater, Fort Lauderdale; Kevin W. Smith, Coral Gables; Scott L. Jahrmarkt, Miami Beach; Scott T. Smith, Miami, all of FL (US)

(73) Assignee: Syntheon, LLC, Miami, FL (US)

( * ) Notice: Subject to any disclaimer, the term of this patent is extended or adjusted under 35 U.S.C. 154(b) by 0 days.

(21) Appl. No.: 09/371,194

(22) Filed: Aug. 10, 1999

(51) Int. Cl.⁷ .................................................. A61N 5/00
(52) U.S. Cl. ........................................ 600/7; 600/8
(58) Field of Search ............................................... 600/1–8

(56) References Cited

U.S. PATENT DOCUMENTS

| | | | |
|---|---|---|---|
| 3,351,049 | 11/1967 | Lawrence | 128/1.2 |
| 3,811,426 | * 5/1974 | Culver et al. | 600/3 |
| 4,323,055 | 4/1982 | Kubiatowicz | 128/1.2 |
| 4,510,924 | * 4/1985 | Gray | 600/8 |
| 4,702,228 | 10/1987 | Russell, Jr. et al. | 128/1.2 |
| 4,784,116 | 11/1988 | Russell, Jr. et al. | 128/1.2 |
| 4,891,165 | 1/1990 | Suthanthiran | 252/633 |
| 4,936,823 | * 6/1990 | Colvin et al. | 600/7 |
| 5,342,283 | 8/1994 | Good | 600/8 |
| 5,405,309 | 4/1995 | Carden, Jr. | 600/3 |
| 5,713,828 | 2/1998 | Coniglione | 600/7 |

* cited by examiner

*Primary Examiner*—John P. Lacyk
(74) *Attorney, Agent, or Firm*—David P. Gordon; David S. Jacobson; Thomas A. Gallagher (57) ABSTRACT

Radioactive therapeutic seeds include a substantially radiotransparent cylindrical capsule provided with a radioactive isotope, a radiopaque marker, and an engagement structure adapted to engage tissue surrounding the seeds at the implant site. The engagement structure is also preferably adapted to releasably engage the inside of a delivery needle prior to implantation. The engagement structure is preferably adapted to prevent axial longitudinal movement and axial rotation of a seed about its longitudinal axis when the seed is implanted. According to a preferred embodiment of the invention, the engagement structure includes three spring elements which are biased away from the seed capsule and which provide positive fixation in the tissue, and also frictionally engage the inside of the needle.

49 Claims, 5 Drawing Sheets

RADIOACTIVE THERAPEUTIC SEEDS HAVING FIXATION STRUCTURE

BACKGROUND OF THE INVENTION

1. Field of the Invention

The invention relates to radioactive therapeutic seeds. More particularly, the invention relates to improved radioactive therapeutic seeds for the treatment of oncological and other medical conditions.

2. State of the Art

Radioactive seed therapy is a well known and well accepted medical procedure for the treatment of various oncological and other medical conditions. Seed therapy, also known as brachytherapy typically involves the implantation of fifty to one hundred tiny capsules (seeds) into or around a treatment site. The capsules contain a radioactive isotope which irradiates the treatment site at close range without adversely affecting other parts of the body. Brachytherapy has been used successfully in the treatment of various types of cancers such as prostate cancer. It has also been used to prevent the growth or regrowth of tissues in the treatment of various occlusive diseases such as arteriosclerosis and arthrosclerosis subsequent to balloon angioplasty.

Radioactive therapeutic seeds are carefully designed to possess several important qualities. First, they are relatively small, typically approximately 0.025 inch in diameter and approximately 0.16 inch long so that they may be implanted using minimally invasive instruments and techniques. Second, the radioactive isotope must be enclosed in a biocompatible protective package since the seeds are typically not removed and will remain in the body for many years. Third, each seed preferably includes a radiopaque (e.g. high Z material) marker so that it can be located at the treatment site with the aid of fluoroscopy. Fourth, the protective package and the radiopaque marker have been designed to not cast "shadows" in the irradiation pattern of the isotope. Fifth, the isotope has been evenly distributed within the protective package so as to avoid any "hot spots" of radiation.

The state of the art of radioactive therapeutic seeds is substantially disclosed in seven U.S. Pat. No. 5,713,828 to Coniglione for "Hollow-Tube Brachytherapy Device", U.S. Pat. No. 5,405,309 to Carden, Jr. for "X-Ray Emitting Interstitial Implants", U.S. Pat. No. 4,891,165 to Suthanthiran for "Device and Method for Encapsulating Radioactive Materials" and U.S. Pat. No. 4,784,116 to Russell, Jr. et al. for "Capsule for Interstitial Implants", U.S. Pat. No. 4,702,228 to Russell, Jr. et al. for "X-Ray Emitting Interstitial Implants", U.S. Pat. No. 4,323,055 to Kubiatowicz for "Radioactive Iodine Seed", and U.S. Pat. No. 3,351,049 to Lawrence for "Therapeutic Metal Seed Containing within a Radioactive Isotope Disposed on a Carrier and Method of Manufacture".

The Lawrence patent describes many of the essential features of radioactive therapeutic seeds. Lawrence describes radioactive isotopes (I-125, Pd-103, Cs-131, Xe-133, and Yt-169) which emit low energy X-rays and which have relatively short half-lives. When implanted at a treatment site, these isotopes provide sufficient radiotherapy without posing a radiation danger to the medical practitioner (s), people in the vicinity of the patient, or other parts of the patient's body. Lawrence further describes a protective capsule which contains the isotope and prevents the isotope from migrating throughout the body where it might interfere with healthy tissue. The capsule is cylindrical and made of low atomic number biocompatible materials such as stainless steel or titanium which substantially do not absorb X-rays. The isotope is coated on a rod shaped carrier made of similar X-ray transparent (e.g. low Z) material, placed inside the capsule cylinder along with a radiopaque marker wire, and the ends of the capsule cylinder are closed.

In 1980, Kubiatowicz made a minor improvement in the basic Lawrence design by providing that the entire isotope carrier be made of radiopaque material such as silver. Kubiatowicz recognized that since the isotope was carried on the entire outer surface of the carrier, there was no need to make the carrier body X-ray transparent as suggested by Lawrence. The larger radiopaque carrier body described by Kubiatowicz makes the seeds easier to see with X-ray or fluoroscopic examination.

Several years later, Russell, Jr. et al., in U.S. Pat. Nos. 4,707,228 and 4,784,116, explained that the capsule design of Lawrence and Kubiatowicz produces anisotropic angular radiation distribution. According to Russell, Jr. et al., the shell forming techniques used in the Lawrence-type seeds result in large beads of shell material at the ends of the seeds. These beads substantially shield radiation thereby casting undesirable shadows in the longitudinal ends of the irradiation pattern of the isotope. Russell, Jr. et al. proposed a new seed design to solve this problem. In particular, Russell, Jr. et al. proposed a seed having a cylindrical container which is sealed with end caps which have a wall thickness that is substantially the same as the wall thickness of the cylindrical container. The end caps are attached to the cylindrical container by welding or crimping.

An alternate solution to the non-uniform radiation pattern of the Lawrence type seeds was proposed by Suthanthiran in U.S. Pat. No. 4,891,165. Suthanthiran's solution was to form a seed capsule from two interfitting sleeves, each having one open end and one closed end. The thickness of the sleeve side walls and their closed ends is such that when the sleeves are interfit in an overlapping manner, the total side wall thickness of the assembled capsule is approximately equal to the end wall thickness.

Despite the fact that radioactive therapeutic seeds have been in use for over thirty years and despite the several significant improvements made in these seeds, many concerns still exist regarding their design and construction.

Due to the general manner in which brachytherapy seeds are implanted, there exists the possibility that the seeds may migrate during implantation and post-operatively. Seeds are typically delivered to a treatment site by loading a plurality of seeds into a needle having an open distal end and an obturator extending into the proximal end of the needle proximal of the seeds. The needle must be handled with care to prevent the seeds from falling out of the open distal end of the needle as they are inclined to do if the distal end of the needle is tilted downward. The needle is then inserted into the patient to the farthest implant site. The needle is then slowly withdrawn while maintaining the obturator at its current location such that the needle moves proximally relative to the obturator and the seeds. The seeds are thereby released from the needle at the intended location. This difficult maneuver often results in some proximal movement of the obturator relative to the implant site which creates a negative pressure between the obturator and the seeds. The negative pressure can unintentionally draw properly positioned cylindrical seeds away from their intended implant site. Additionally, depending upon the locus of implantation, seeds may also unintentionally migrate after the implantation procedure. The consequences of unintended seed movement can be serious. First, the tissue requiring treatment may not receive the prescribed radiation dose. Second, healthy tissues may be dosed with radiation to the extent that the healthy tissues become damaged. Therefore, there is an important, yet unresolved, issue with respect to immobilizing a seed at the desired implant site.

In addition, as discussed with respect to the patents of the prior art, the art of brachytherapy seeds has had a longstanding focus on creating seeds having an isotropic radiation distribution; i.e., a longitudinally uniform radiation distribution. This is not surprising, particularly because the physician has had no way of controlling the rotational orientation of the seed in the body of the patient. Moreover, even if rotational control were not a problem, no prior art has addressed the value of a radially non-uniform radiation distribution. However, if it were possible to control the orientation of a seed within the body and ensure that the seed did not unintentionally move radially or axially about its longitudinal axis after implantation, a seed purposefully configured for a radially non-uniform radiation distribution would be a valuable tool in brachytherapy treatment.

SUMMARY OF THE INVENTION

It is therefore an object of the invention to provide radioactive therapeutic seeds which have means for engaging the tissue surrounding the seeds when the seeds are implanted.

It is also an object of the invention to provide radioactive therapeutic seeds which have means for engaging the internal walls of the needle to prevent unintended dislodging of the seeds from the needle, yet which permits the seeds to be purposefully deployed when intended.

It is another object of the invention to provide radioactive therapeutic seeds which have a radially non-uniform radiation distribution.

It is a further object of the invention to provide radioactive therapeutic seeds which have means for maintaining a particular axial orientation of the seeds within the tissue at the implant site such that a radially non-uniform radiation distribution can effectively be used to primarily irradiate selected tissue and minimally irradiate other tissue.

In accord with these objects which will be discussed in detail below, the radioactive therapeutic seeds of the present invention include a substantially radiotransparent cylindrical capsule provided with a radioactive isotope, preferably a radiopaque marker, and an engagement means. The engagement means is preferably adapted to positively engage tissue surrounding the seeds at the implant site and is also preferably adapted to releasably engage, e.g., frictionally engage, the inside of the needle prior to implantation. The engagement means is also preferably adapted to prevent axial rotation of a seed about its longitudinal axis once deployed. According to a preferred embodiment of the invention, the engagement means includes three spring elements which are biased away from the seed capsule and which provide positive fixation in the tissue, and also frictionally engage the inside of the needle. According to another embodiment of the invention, the engagement means includes a material over at least a portion of the outside of a seed which expands when in contact with moisture.

The engagement means positively engages the tissue and thereby fixes each seed longitudinally at its location and in its deployed radial orientation. Therefore, during deployment of the seeds, any negative pressure built up between the seeds and the obturator does not cause movement of the seeds. Additionally, the seeds are prevented from migrating post-operatively. Furthermore, as the engagement means of the seeds are adapted to prevent axial rotation of the seed, a seed can be advantageously configured to provide a radially non-uniform radiation distribution which can be oriented to irradiate selected tissues and shield from radiation other tissues surrounding the seed.

According to another aspect of the invention, the ends of the seed capsule may be provided with connectors which can be coupled to discrete spacing links to linearly align a plurality of seeds. The spacing links may also be provided with engagement means which engages the tissue and thereby fixes each spacing link longitudinally at its location. The capsules and links can be aligned end to end to facilitate deployment and desirable relative spacing, and fixation of the capsules at the locus of treatment.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1A:
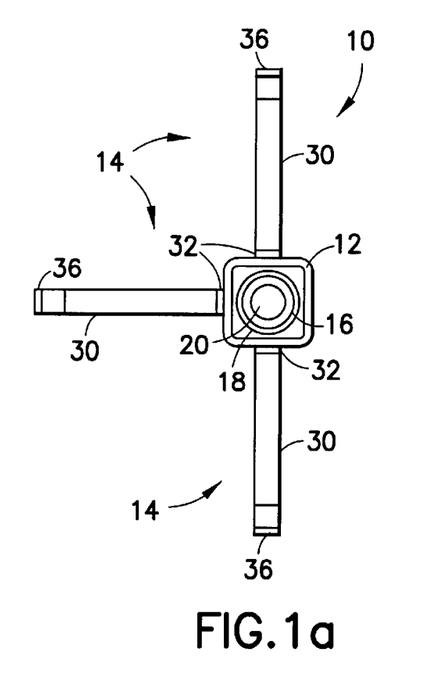
FIG. 1a is an enlarged schematic cross section of a first embodiment of a radioactive therapeutic seed having one embodiment of an engagement means according to the invention, the engagement means shown in an expanded state.
Figure 1B:
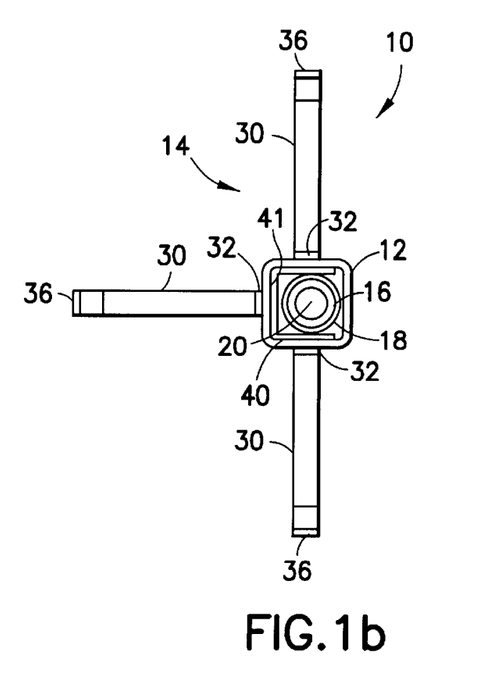
FIG. 1b is an enlarged schematic cross section of a second embodiment of a radioactive therapeutic seed having an engagement means according to the invention, the engagement means shown in an expanded state.

Referring now to FIGS. 1a and 1b, according to the invention, a radioactive therapeutic seed 10 includes a capsule 12 having an engagement means 14, which will be described in detail below, for engaging tissue at the seed implant location. The capsule 12 is provided with a carrier 16 on which a radioactive isotope coating 18 is provided, and preferably a radiopaque marker 20. Alternatively, the marker 20 can be made from a diamagnetic or paramagnetic substance, e.g., gadolinium metal or salt, to permit visualization of the seed with magnetic resonance imaging (MRI). The capsule is preferably made from titanium, aluminum, plastic, or another radiotransparent (low Z) material. The terms "radiotransparent", "radiolucent", "radiotranslucent", and "low Z" are used interchangeably herein. The construction of the capsule 12 and the relative configuration and arrangement of the carrier 16, radioactive isotope 18, and marker 20 may be any known in the art. Several preferred arrangements are disclosed in co-owned and co-pending U.S. Ser. No. 09/133,081, U.S. Ser. No. 09/133,072, U.S. Ser. No. 09/200,698, and U.S. Ser. No. 09/312,215, which are hereby incorporated by reference herein in their entireties.

Figure 2:
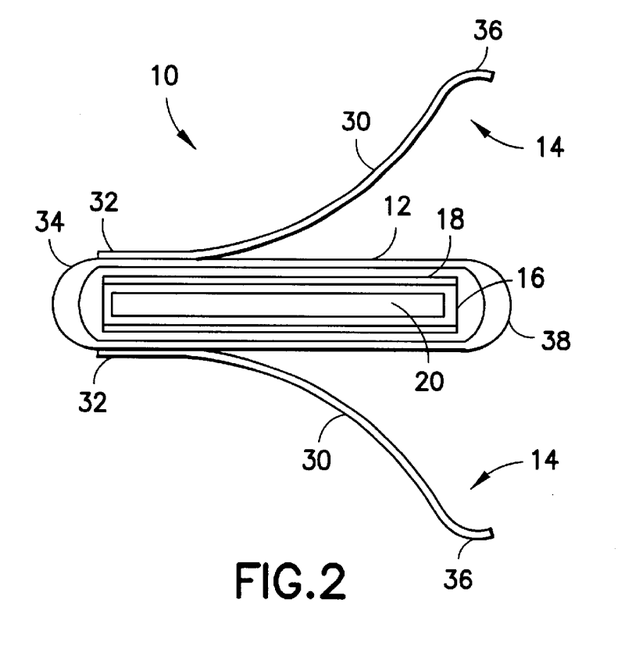
FIG. 2 is an enlarged schematic longitudinal section of the radioactive therapeutic seed of FIG. 1b, the engagement means shown in an expanded state.
Figure 3:
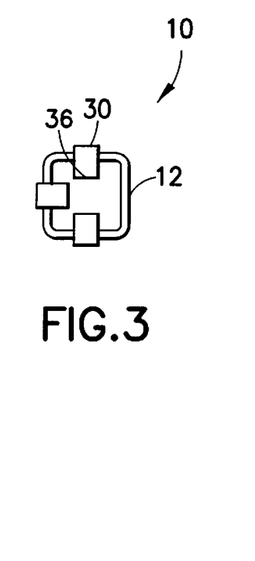
FIG. 3 is an end view of a radioactive therapeutic seed according to the invention, with the engagement means shown in a contracted state.
Figure 4:
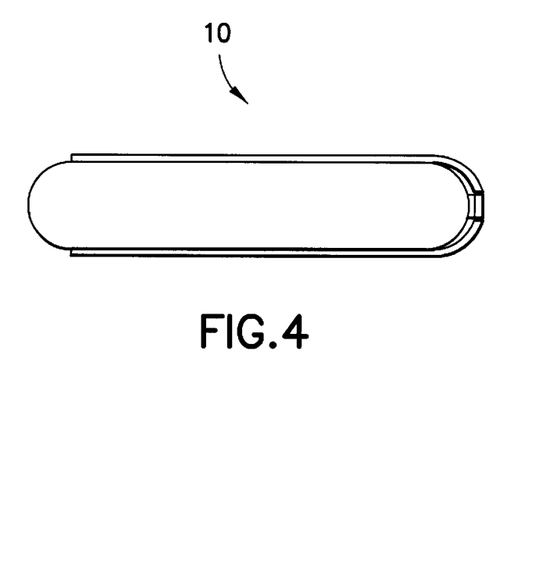
FIG. 4 is a side elevation view of a radioactive therapeutic seed according to the invention, with the engagement means shown in a contracted state.

The engagement means 14 is preferably three resilient spring members 30 having one end 32 attached to a first end 34 of the capsule and having a free end 36 biased away from the capsule. The members 30 are radially spaced about the exterior of the capsule 12. Referring to FIGS. 3 and 4, the members 30 are preferably shaped such that when the free ends 36 are forced towards the second end 38 of the capsule 12, the members 30, along their length, contour to the exterior of the capsule. However, turning back to FIGS. 1 and 2, when the members 30 are permitted to expand away from the second end 38 of the capsule 12, in accord with their bias, they each form a barb-like structure which substantially resist axial movement of the seed within tissue, particularly in the direction of the second end of the capsule. In addition, the barb-like structures resist radial movement within the tissue as they are radially spaced about the capsule.

Figure 5:
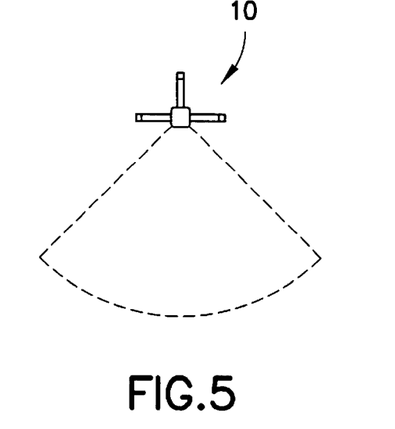
FIG. 5 is an end view of the radioactive therapeutic seed according to the invention having an optional first radially nonuniform radiation distribution.
Figure 6:
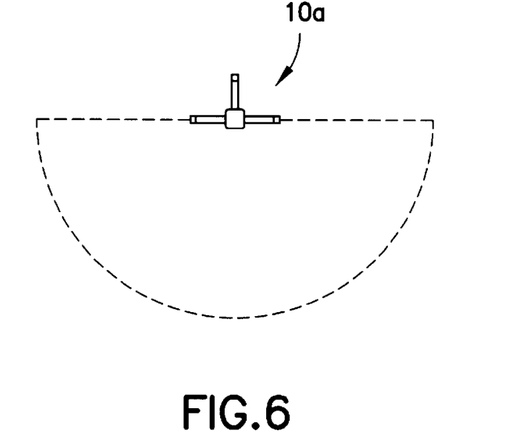
FIG. 6 is an end view of a radioactive therapeutic seed according to the invention having an optional second radially nonuniform radiation distribution.
Figure 7:
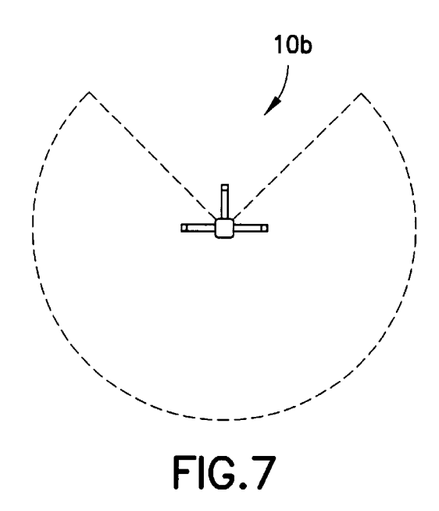
FIG. 7 is an end view of a radioactive therapeutic seed according to the invention having an optional third radially nonuniform radiation distribution.

According to a preferred aspect of the invention, the radioactive isotope 18 may optionally be provided or shielded to have reduced radiation transmission through the capsule 12 in one or more radial arcs. For example, as seen in the embodiment of FIG. 1b, a radiopaque coating 40 may be provided on a portion of the interior surface 42 of the capsule 12, thereby substantially preventing radiation transmission through the capsule at that portion. FIG. 5 illustrates in dotted line the extent, e.g., through a 90° arc, of the radiation cloud outside a seed 10 configured as shown in FIG. 1b. Alternatively, a physical radiopaque barrier may be provided between the carrier and a portion of the capsule. As yet another alternative, the radioactive isotope 18 may be provided to only a radial portion of the exterior surface of the carrier 16 (less than the entire circumference of the exterior surface) or, in lieu of a carrier, the radioactive isotope may be provided directly to a radial portion of a side of the inner surface of the capsule between the first and second ends of the capsule. It will be appreciated that other radially non-uniform distribution clouds can be configured based upon the extent of the shielding and/or the arrangement of the radioactive isotope on the carrier 16 or inner surface of the capsule. For example, FIG. 6 illustrates a seed 10a having a 180° radial radiation distribution cloud, and FIG. 7 illustrates a seed 10b having a 270° radial radiation distribution. Other alternatives for configuring seeds to radially directionally transmit radiation are disclosed in U.S. Ser. No. 09/133,081, which has previously been incorporated herein in its entirety. Therefore, regardless of the alternative, the resulting seed 10 can be configured to transmit radiation through a predetermined arc greater than 0° and less than 360° around the axis of the seed.

Figure 8:
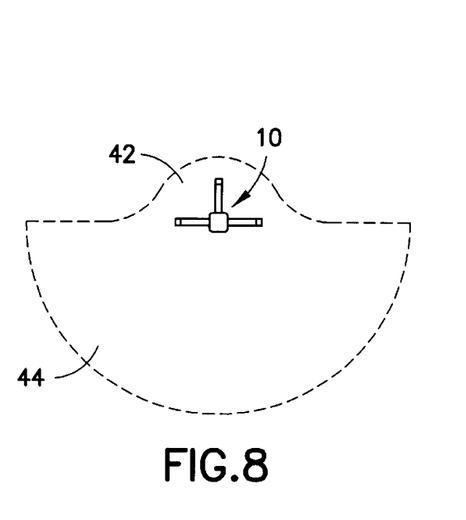
FIG. 8 is an end view of a radioactive therapeutic seed according to the invention having first radial radiation distribution and a second radial radiation distribution different than said first radial radiation distribution.

Turning now to FIG. 8, it will be appreciated that the seed 10 may be configured to transmit two different levels 42, 44 of radiation in two different directions. For example, a shielding which permits a reduced radiation transmission, rather than substantially complete radiopacity, may be utilized to create the transmission level 42. Moreover, a plurality of shielding members, having the same or different levels of radiation transmission reduction may be radially spaced within the capsule. The result of all of the above embodiments is that the radiation transmission of the seed is capable of being radially anisotropic relative to a point on the longitudinal axis of the capsule.

In addition, the arrangement of three spring members 30 which are not equally spaced about the capsule (i.e., which are not separated at 120°) can be used to correspond to and visually indicate the relative directions of shielding and/or radiation transmission. For example, in FIG. 1, the central spring member (i.e., that member located 90° from each of the other members) may indicate that the radiation transmission is constrained to transmit opposite that central member. Alternatively, indicia, e.g., a colored line, may be provided to the exterior of the seed.

Figure 9:
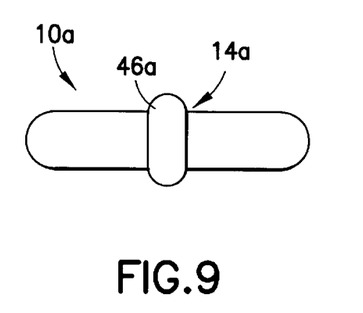
FIG. 9 is an enlarged side elevation of a second embodiment of a radioactive therapeutic seed having a second embodiment of an engagement means according to the invention, the engagement means shown in an unexpanded state.
Figure 10:
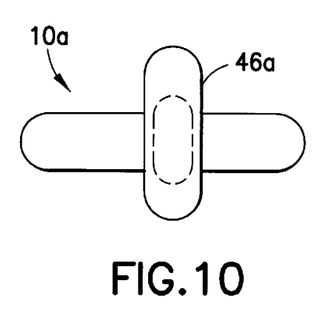
FIG. 10 is a view similar to FIG. 9 with the engagement means shown in an expanded state.

Referring now to FIGS. 9, a seed 10a according to another embodiment of the invention is provided with an engagement means 14a including material which expands when exposed to moisture. The engagement means 14a is preferably a ring 46a of hydrophobic material, e.g., urethane, or other expandable plastic material which causes the ring to enlarge when exposed to moisture within the human body (FIG. 10). When the engagement means expands, the engagement means extends into the body tissue and facilitates longitudinal fixation of the seed at its implanted location. It will be appreciated that other configurations of the expandable material, e.g., one or more laterally extending prongs, may be used to provide rotational fixation as well as longitudinal fixation.

Figure 11:
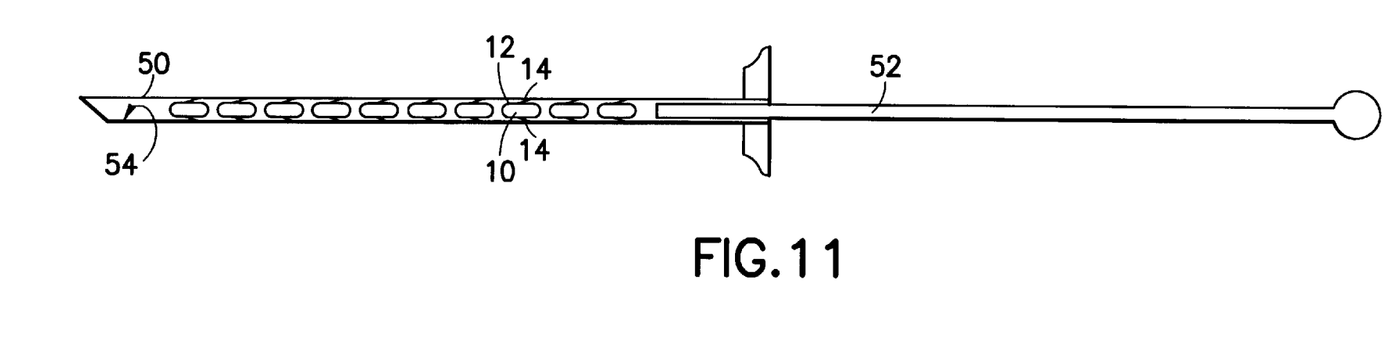
FIG. 11 is a longitudinal section of a therapeutic seed delivery system according to the invention.

Turning now to FIG. 11, in use, a plurality of the seeds 10 may be loaded into a delivery needle 50 having a proximal obturator 52. The engagement means 14 on the capsules 12 of the seeds 10 press against, and frictionally engage, the internal wall 54 of the needle 50 to maintain the seeds within the needle unless forcibly moved therefrom. The needle is inserted into the patient to the farthest implant site. The needle is then withdrawn while maintaining the obturator at its current location such that the needle moves proximally relative to the obturator and releases the seeds from the needle at the intended location. As the seeds are released, the engagement means expand and positively engage the tissue at their respective release sites. As a result, even if there is some proximal movement of the obturator relative to the implant site, any negative pressure created between the obturator and the seeds will not overcome the engagement of the seeds in the tissue, and the seeds remain at their intended location. Moreover, after implantation, the engagement means prevents seed migration.

Additionally, as the seeds have the ability to be both axially and radially fixed at an implant location, a seed can be provided with a radiation source which is configured to provide a radially non-uniform radiation distribution and can be oriented and maintained at a particular orientation to irradiate selected tissues and shield from radiation other tissues surrounding the seed.

Figure 12:
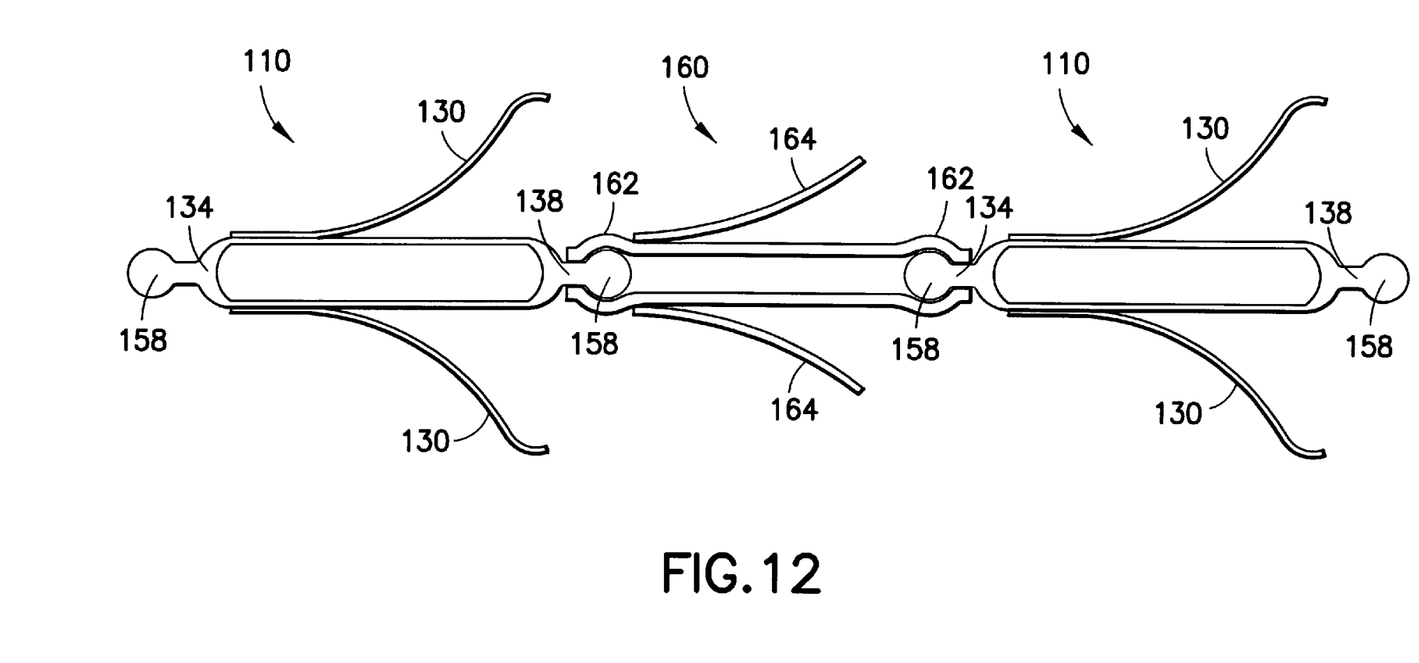
FIG. 12 is a schematic view of two radioactive therapeutic seeds coupled by a spacing link having an engagement means according to the invention, with the engagement means shown in a expanded state.

Referring now to FIG. 12, according to another aspect of the invention, seeds 110, optionally having engagement means such as springs 130 described above, may be provided with connectors 158 at the ends 134, 138 thereof. The connectors 158, e.g., spherical or flattened balls, are adapted to couple with discrete spacing links 160 to linearly align and hold together a plurality of seeds. The spacing links are preferably made of a stiff, optionally hollow, bioabsorbable polymer, e.g., polydioxanone, poly(1-lactide-co-trimethylene carbonate), d,1-lactide/caprolactone or 50:50 d,1-polylactide co-glycolide polymer. The spacing links 160 include connectors 162, e.g., resilient tubular forms, adapted to interlock (or otherwise couple) with the connectors 158 on the seeds 110. Other connectors 158, 162 for both the seeds 110 and the spacing links 160 are disclosed in U.S. Ser. No. 09/312,215, which has previously been incorporated by reference herein in its entirety. The spacing links preferably also include an engagement means, e.g., springs 164, which engages the tissue and thereby fixes each spacing link 160 longitudinally at its location. The seeds 110 and links 160 (together a "seed system") can be aligned end to end to facilitate deployment, desirable relative spacing, and fixation of the seeds at the locus of treatment.

Figure 13:
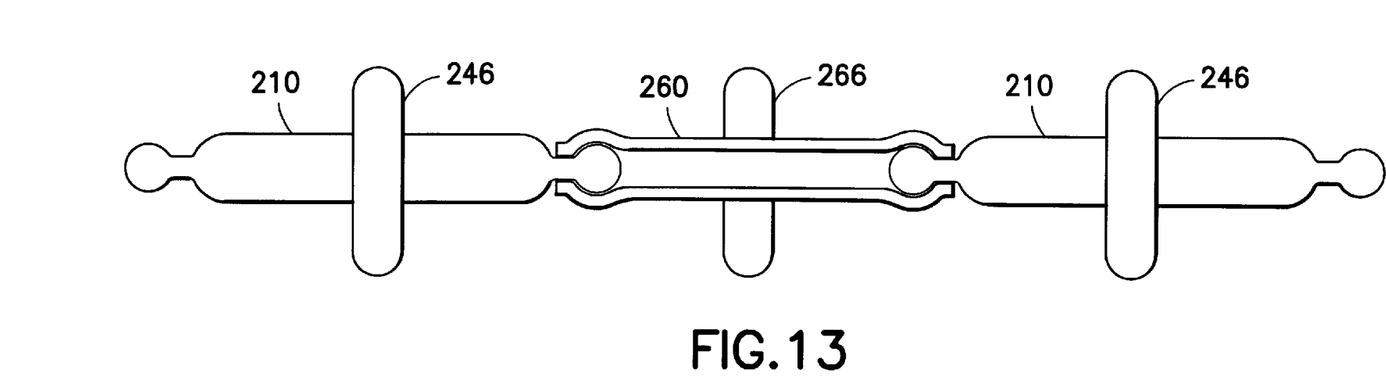
FIG. 13 is a schematic view of two radioactive therapeutic seeds coupled by a spacing link having another engagement means according to the invention, with the engagement means shown in a expanded state.

Turning now to FIG. 13, another seed system including seeds 210 connected to a spacing link 260 is shown. The seeds have a moisture expandable engagement means 246 and the spacing link have a moisture expandable engagement means 266, which facilitates fixation of the seeds and the spacing links within the tissue of the body.

There have been described and illustrated herein several embodiments of a radioactive therapeutic seed. While particular embodiments of the invention have been described, it is not intended that the invention be limited thereto, as it is intended that the invention be as broad in scope as the art will allow and that the specification be read likewise. Also, while the preferred engagement means includes three resilient spring members, the engagement means may includes one, two, or more than three members. In addition, the resilient members may be radially spaced equally or unequally about the capsule. Furthermore, while the resilient members have been shown attached at one end of the capsule, they may be attached at one or more axial locations on the capsule. Moreover, while one particular engagement means has been described, it will be appreciated that other embodiments of an engagement means may be used. For example, any barb-like structure (resilient, non-resiliently flexible, or rigid) or any resiliently expandable structure may be used to engage the tissue and/or the needle. Also, while the radiation reducing or shielding elements have been shown located on the interior of the capsule, it will be appreciated that such a radiation reducing or shielding element may be placed on the exterior of the capsule. For example, a substantially radiopaque coating, e.g., a biocompatible gold paint, may be provided to the exterior surface of the capsule. In addition, while the seed has been shown to have a generally rectangular cross-section, it will be appreciated that the seed may likewise be provided with a generally circular cross-section. Also, while a seed having a male connector and a spacing link having a female connector is described, it will be appreciated that a seed having a female connector and a spacing link having a male connector can likewise be used. It will therefore be appreciated by those skilled in the art that yet other modifications could be made to the provided invention without deviating from its spirit and scope as so claimed.

What is claimed is:

1. A radioactive therapeutic seed for implantation into human tissue, comprising:

a radiolucent, substantially rigid, tubular capsule provided with a radioactive isotope and having an engagement means for automatically positively engaging the tissue.

2. A radioactive therapeutic seed according to claim 1, wherein:

said engagement means substantially prevents axial movement of said seed in the tissue.

3. A radioactive therapeutic seed according to claim 1, wherein:

said engagement means substantially prevents axial rotation of said seed in the tissue.

4. A radioactive therapeutic seed according to claim 1, wherein:

said engagement means includes at least one barb.

5. A radioactive therapeutic seed according to claim 1, wherein:

said engagement means includes at least one resilient member.

6. A radioactive therapeutic seed according to claim 5, wherein:

said capsule has an exterior, and said at least one resilient member is compressible against said exterior.

7. A radioactive therapeutic seed according to claim 5, wherein:

said engagement means includes three resilient members.

8. A radioactive therapeutic seed according to claim 5, wherein:

said engagement means includes at least three resilient members which are unequally radially spaced about said capsule.

9. A radioactive therapeutic seed according to claim 1, wherein:

said engagement means includes at least one spring member.

10. A radioactive therapeutic seed according to claim 1, wherein:

said engagement means includes a moisture expandable element.

11. A radioactive therapeutic seed according to claim 1, wherein:

said capsule has a longitudinal axis, and said radiation is transmitted through said capsule radially anisotropically relative to a point on said longitudinal axis.

12. A radioactive therapeutic seed according to claim 1, wherein:

said capsule has a longitudinal axis, and said radioactive isotope is arranged to distribute radiation through an arc less than 360° about said longitudinal axis.

13. A radioactive therapeutic seed according to claim 1, wherein:

said capsule includes means for attenuating said radiation transmission through a radial portion of said capsule.

14. A radioactive therapeutic seed according to claim 13, wherein:

wherein said means for attenuating substantially completely prevents transmission of radiation through said radial portion.

15. A radioactive therapeutic seed according to claim 13, wherein:
said means for attenuating includes a substantially radiopaque element provided between said radioactive isotope and said radial portion of said capsule.

16. A radioactive therapeutic seed according to claim 13, wherein:
said means for attenuating includes a radiopaque coating provided along an interior surface of said portion of said capsule.

17. A radioactive therapeutic seed according to claim 1, wherein:
said capsule further comprises at least one of a radiopaque marker and an MRI-visible marker.

18. A radioactive therapeutic seed for implantation into human tissue, comprising:
a) a capsule having a longitudinal axis, said capsule provided with a radioactive isotope and adapted such that radiation transmitted from said capsule is radially anisotropic relative to a point on said longitudinal axis; and
b) a means for preventing rotation of said seed once deployed in the human tissue.

19. A radioactive therapeutic seed according to claim 18, wherein:
said capsule is adapted for radially anisotropic radiation transmission by providing said capsule with a shielding means for reducing a level of radiation transmitted through said capsule relative to a level of radiation emission by said radioactive isotope.

20. A radioactive therapeutic seed according to claim 19, wherein:
said capsule has an inner surface, and said shielding means is situated between said inner surface and radioactive isotope.

21. A radioactive therapeutic seed according to claim 19, wherein:
said shielding means is a substantially radiopaque coating provided on a portion of said an inner surface of said capsule.

22. A radioactive therapeutic seed according to claim 18, further comprising:
c) a carrier structure having first and second ends and a side surface between said first and second ends, said side surface defining a perimeter, and said radioactive isotope provided on said side surface about less than an entirety of said perimeter, and
said capsule has an interior and said carrier structure is provided in said interior of said capsule.

23. A radioactive therapeutic seed according to claim 18, wherein:
said capsule has a surface including first and second ends and a side surface extending between said first and second sides and defining a circumference, and said radioactive isotope is provided on said side surface about less than an entirety of said circumference.

24. A radioactive therapeutic seed according to claim 18, wherein:
said capsule has a surface including first and second ends and a side surface extending between said first and second sides and defining a circumference, and said capsule is adapted for radially anisotropic radiation transmission by providing to said side surface about less than an entirety of said circumference a substance which attenuates radiation transmission.

25. A radioactive therapeutic seed according to claim 18, wherein:
said radially anisotropic radiation transmission includes a first radial arc through which radiation is substantially prevented from being transmitted.

26. A radioactive therapeutic seed according to claim 18, wherein:
said radially anisotropic radiation transmission includes a first radial arc through which a first level of radiation is transmitted and a radial arc through which a second level of radiation is transmitted, said second level being lower than said first level.

27. A delivery system for implanting radioactive therapeutic seeds at an implant site, comprising:
a) a hollow tube having proximal and distal ends and an interior surface; and
b) a plurality of seeds loaded into said tube, each said seed including a radiation source and including an engagement means for engaging said interior surface of said tube such that said seeds do not exit the tube unless forced therefrom.

28. A delivery system according to claim 27, further comprising:
c) an obturator located in said proximal end of said tube, proximally of said plurality of seeds,
wherein when tube is moved proximally relative to said obturator, said plurality of seeds are forcibly released from said tube.

29. A delivery system according to claim 27, wherein:
said engagement means is a plurality of flexible members.

30. A delivery system according to claim 29, wherein:
said flexible members are resilient.

31. A delivery system according to claim 27, wherein:
said engagement means includes a moisture-expandable element.

32. A delivery system according to claim 27, wherein:
each said capsule has a longitudinal axis, and said radiation is transmitted through each said capsule radially anisotropically relative to a point on said longitudinal axis.

33. A delivery system according to claim 27, wherein:
each said capsule has a longitudinal axis, and said radiation source is arranged to distribute radiation through an arc less than 360° about said longitudinal axis.

34. A delivery system according to claim 27, wherein:
said capsule includes means for attenuating transmission through a first radial portion of said capsule radiation emitted by said radiation source relative to a second radial portion.

35. A delivery system according to claim 34, wherein:
wherein said means for attenuating substantially completely prevents transmission of radiation through said first radial portion.

36. A radioactive therapeutic seed system for implantation into human tissue, comprising:
a) at least one seed, said at least one seed comprising a biocompatible capsule having a first end and a second end, said first end having a first connecting structure and said second end having one of a second connecting structure, said capsule provided with a radioactive isotope; and
b) a discrete linking member adapted to interlock with at least one of said first and second connecting structures and having an engagement means for positively engaging the tissue.

37. A radioactive therapeutic seed system according to claim 36, wherein:

said linking member is bioabsorbable.

38. A radioactive therapeutic seed system according to claim 36, wherein:

said linking member is tubular.

39. A radioactive therapeutic seed system according to claim 36, wherein:

said engagement means includes at least one spring member.

40. A radioactive therapeutic seed system according to claim 36, wherein:

said engagement means includes a moisture-expandable element.

41. A radioactive therapeutic seed system according to claim 36, wherein:

each said seed includes an engagement means for positively engaging the tissue.

42. A linking member for linking two radioactive therapeutic seeds, each seed including a biocompatible capsule having a first end and a second end, the first end having a first connecting structure and the second end having one of the first connecting structure and a second connecting structure, said linking member, comprising:

a body having a first means for interlocking with the first connecting structure, a second means for interlocking with the one of the first connecting structure and the second connecting structure, and an engagement means for positively engaging the tissue.

43. A linking member according to claim 42, wherein:

said engagement means includes at least one resilient member.

44. A linking member according to claim 42, wherein:

said engagement means includes a moisture-expandable element.

45. A radioactive therapeutic seed for implantation into human tissue, comprising:

a substantially rigid radiolucent capsule provided with a cavity lying along a longitudinal axis of said capsule and containing a radioactive isotope, said capsule having an engagement means for automatically positively engaging the tissue.

46. A radioactive therapeutic seed according to claim 45, wherein:

said cavity is provided with permanently closed ends.

47. A radioactive therapeutic seed according to claim 45, wherein:

said engagement means includes a plurality of resilient members which are not evenly spaced about said capsule.

48. A radioactive therapeutic seed according to claim 1, wherein:

said cavity is provided with permanently closed ends.

49. A radioactive therapeutic seed according to claim 1, wherein:

said engagement means includes a plurality of resilient members which are not evenly spaced about said capsule.

* * * * *